United States Patent [19]

Finnieston

[11] 4,436,088

[45] Mar. 13, 1984

[54] UPPER ARM BRACE

[76] Inventor: Alan Finnieston, 1901 NW. 17 Ave., Miami, Fla. 33125

[21] Appl. No.: 299,815

[22] Filed: Sep. 8, 1981

[51] Int. Cl.³ ............................................. A61F 5/04
[52] U.S. Cl. ...................................... 128/77; 128/90; 128/133
[58] Field of Search ................. 128/77, 83, 84 R, 85, 128/87 R, 89 R, 89 A, 90, 94, 157, 165, 169, 171, 133; 273/189 R, 189 A; 2/16

[56] References Cited

U.S. PATENT DOCUMENTS

| | | | |
|---|---|---|---|
| 1,375,507 | 4/1921 | Grundmann | 128/83 |
| 3,074,723 | 1/1963 | Esty | 128/133 X |
| 3,563,234 | 2/1971 | Umstead | 128/90 |
| 3,658,345 | 4/1972 | Siggson | 273/189 A |
| 3,811,434 | 5/1974 | Jacobson et al. | 128/89 R |
| 4,027,666 | 6/1977 | Marx | 273/189 R X |
| 4,048,991 | 9/1977 | Marx | 128/77 X |

FOREIGN PATENT DOCUMENTS

| | | | |
|---|---|---|---|
| 542305 | 4/1956 | Italy | 128/87 R |
| 765213 | 1/1957 | United Kingdom | 128/157 |

Primary Examiner—Lee S. Cohen
Assistant Examiner—Angela D. Sykes
Attorney, Agent, or Firm—Larson and Taylor

[57] ABSTRACT

An upper arm brace to be secured about the upper arm of a wearer in two parts, a posterior segment and an anterior segment. The two segments intermate in a clam shell type embrace about the arm of a wearer to lend support to it; the segments are held in mated relation by a plurality of straps.

3 Claims, 4 Drawing Figures

UPPER ARM BRACE

FIELD OF THE INVENTION

This invention relates to an upper arm brace.

BACKGROUND OF THE INVENTION

In the past there have been numerous types of devices which have been utilized for a person having an injured or broken arm such as the well known plaster cast. This invention is of an upper arm brace which is adapted to be secured about the arm of wearer and wherein a posterior and an anterior segment are provided for clamping or clam shell type interengagement with one another about the arm of the wearer to apply pressure to the flesh to support the upper arm. The device includes a fastening means and adjustment means to adjust and maintain the amount of pressure which is applied by the two segments when in nested relations which one another and about the arm of a wearer. The segments have contoured surfaces to nest comfortably along the bicep as well as a cut away segment area at the end of the arm brace adjacent to the armpit to allow for full range of movement of the upper arm.

OBJECTS OF THE INVENTION

It is a general object of this invention to provide an upper arm brace comprising a posterior segment and an anterior segment which intermate with one another and which are maintained in position by keeper means which may be in the form of a strap preferably of velcro, secured to the posterior segment.

It is another object of this invention to provide an upper arm brace of the type set forth wherein the base of a posterior segment is provided with a flat surface to apply pressure to the flesh in the posterior side of the arm of a wearer to exert a stabilizing support to an upper arm about which the brace is secured.

It is another object of this invention to provide an upper arm brace of the type set forth wherein the base of the U-shaped anterior segment is provided with a contour surface to apply pressure to the flesh over the bicep of a wearer and to allow some mobility in this area.

It is another object of this invention to provide an upper arm brace of the type set forth wherein the upper end of the arm brace adjacent the armpit is cut away to allow for maximum height at the outer shoulder and to rest comfortably under the arm pit to allow for maximum comfort, protection, and mobility.

It is another object of this invention to provide a brace of the type described wherein a plurality of perforations are provided in a posterior and anterior segment to accommodate breathing and use of the device.

It is another object of this invention to provide a device of the type described wherein a liner means is provided along the anterior segment to provide a padding along the bicep of a user and preferably wherein there is an adjustment means provided to adjust the force exerted by the segments when in telescoping relation with one another, that is with the interior brace received within the posterior brace and in tight clamping relation about the arm of a wearer.

In accordance with these and other objects which will become apparent hereinafter, the instant invention will now be described with reference to the accompanying drawings:

DESCRIPTION OF THE PREFERRED EMBODIMENT

Figure 1:
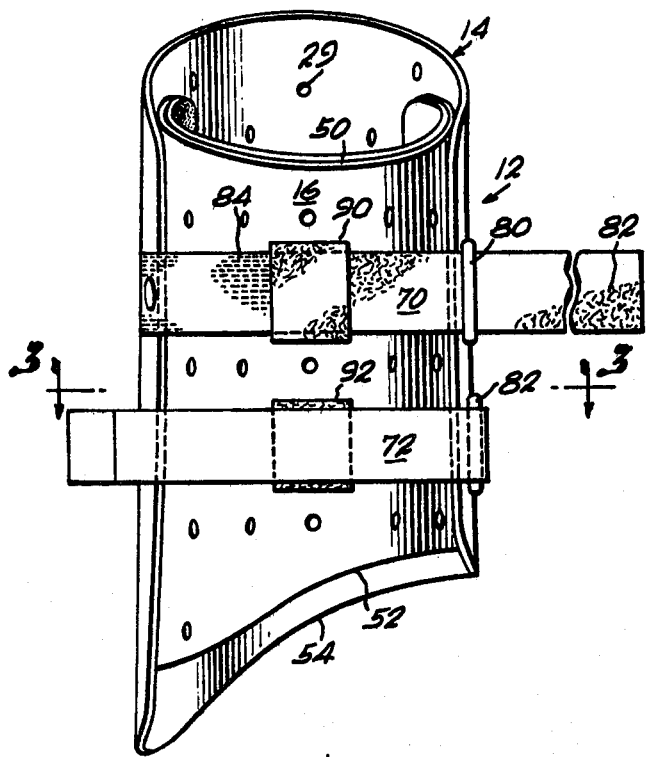
FIG. 1 is a front elevation view of the upper arm brace.

Referring to the drawing wherein like reference characters designate like or corresponding parts throughout the several views and referring particularly to the upper arm brace generally designated by the numeral 12. It is composed of a posterior segment 14 and an anterior segment 16 which are intermated into clam shell relation, so that one is slidable with respect to the other, for example, expandable in a horizontal direction, generally as seen in FIG. 3 to accommodate larger and smaller girths of arms so that one size generally, fits all.

Figure 3:
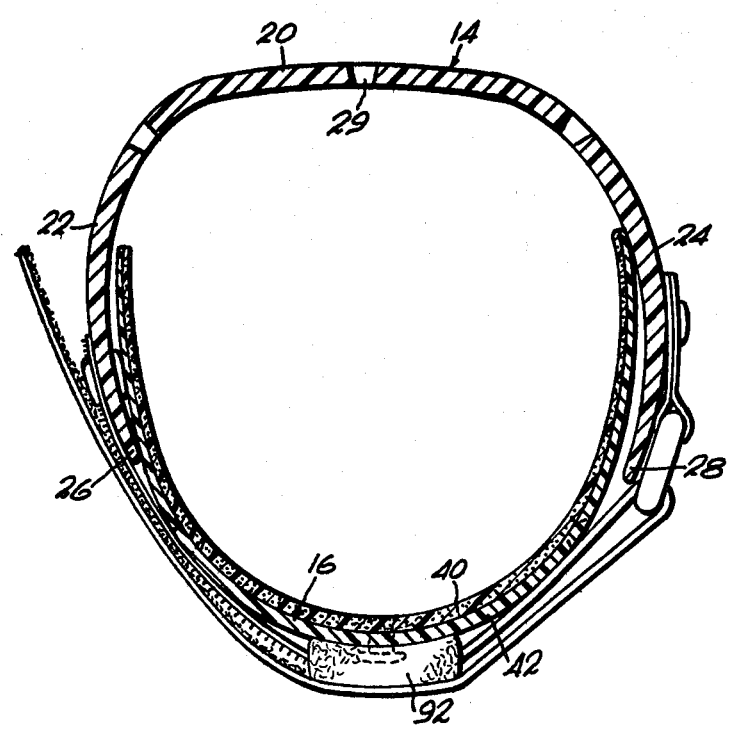
FIG. 3 is a view in cross section taken on the plane indicated by the line 3—3 of the upper arm brace.

Generally speaking, the posterior segment is generally U-shaped in cross section, see FIG. 3, and of a length of about 6 to 8 inches. The base 20 of the U-shaped portion is generally flat and the side walls 22 and 24 are curved smoothly and fairly to spaced terminal ends as at 26 and 28 which are spaced from one another. The lower end of the base 20 is extended beyond the ends of the side walls 20 and 22 as shown at 54 to provide protection for the back of the arm immediately above the elbow. The material is of plastic within the rigid range and is in a flexible relatively thin construction so that the mouth between the terminal ends 26 and 28 can be flexed or expanded by hinged movement of the side walls relative to the base. This segment 14 is perforated as indicated by the holes of which 29 is representative, and which are arranged in a pattern throughout the posterior segment.

Figure 2:
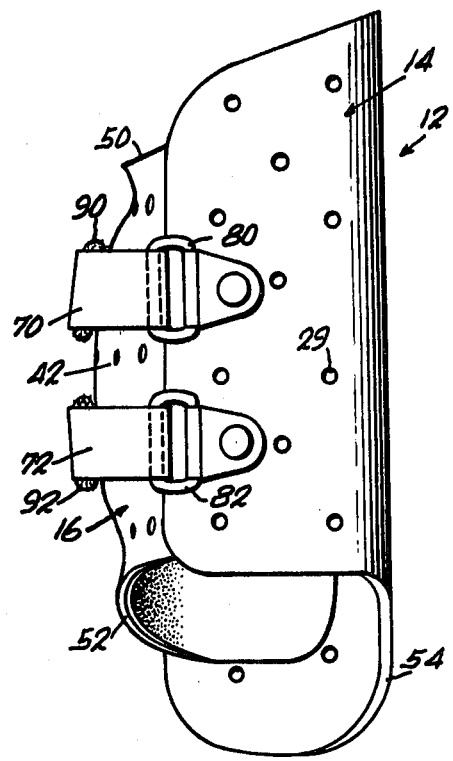
FIG. 2 is a side elevation view of the upper arm brace.
Figure 4:
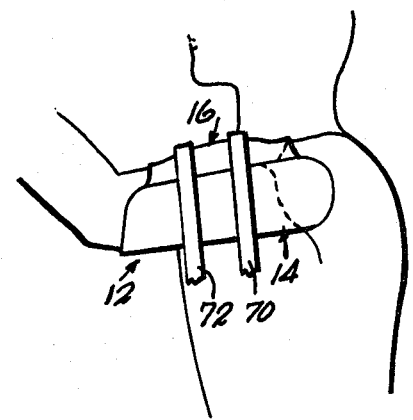
FIG. 4 is a side elevation showing the upper arm brace on the arm of a wearer.

The mating anterior segment is generally designated by the numeral 16; and it is seen that it is generally U-shaped but is somewhat rounded or curved so that as seen in the cross section, it might be considered to be generally C-shaped. It has an outside surface and an inside surface. The inside surface is lined with foam material as is generally designated by the numeral 40. As best seen in FIGS. 2 and 4, the middle cross section is somewhat larger than at the ends, 50 and 52, respectively, so that the brace is somewhat tapered to conform to the arm of a wearer. This outwardly bulged central portion has recessed zones adjacent the upper and lower ends of the bulged central portion so that when the anterior member is in place on the arm it engages the the bicep muscle. This segment is also of rigid plastic material 42 defines a relatively thin plastic skin which is sturdy.

In use, the anterior segment fits over the bicep of the arm of a wearer while the base of the posterior section overlays the muscle along the rear of a wearer's arm. As seen in FIGS. 1,3, and 4, keeper means are provided which may be of a plurality of straps such as 70 and 72. One of each of the straps is adapted to be received in a buckle, such as 80 and 82, fixed along and adjacent one of the mouth edges. The other end of these straps are secured to the oppositel edge 26 by suitable means such as that shown and preferably these straps are of Velcro, each with a portion adjacent one end which comprises J-hooks and another portion which comprises loops to intermate with the J-hooks providing an adjustable strap, as indicated by the numerals 82 and 84.

In any event, once arranged about the arm of a wearer, the straps are tightened. Preferably, the anterior segment includes a plurality of loops, such as that designated by the numerals 90 and 92, which serve to maintain the posterior segment and anterior segment in generally mating relation, resisting relative vertical displacement of the two segments which in position on the arm of a wearer. Thus, there is provided a fastener means or keeper means to maintain the two pieces together in clamped relation about the arm of a wearer.

While this invention has been shown and described in what is considered to be a practical and preferred embodiment, it is recognized that departures may be made within the spirit and scope of this invention which is, therefore, not to be limited except as set forth in the claims which follow within the doctrine of equivalence.

What is claimed is:

1. An upper arm brace for protecting and reinforcing the surfaces of the upper arm of the wearer between the shoulder zone and the elbow zone, said brace comprising, an elongate, generally U-shaped posterior member having a base and sidewalls adapted to extend around the posterior surface of the upper arm, an elongate generally C shaped anterior member having a base and side walls adapted to extend around the anterior surface of the upper arm, the posterior member and the anterior member having longitudinal side edges being disposed in overlapping relationship with each other whereby the anterior and posterior members encase the upper arm with the inner surface of the anterior and posterior members in contact with the surface of the upper arm, said anterior and posterior members being of a semi-rigid material with the side walls of said members capable of being flexed, the base of the anterior member having a central portion bulged outwardly to accommodate the bicep muscle whereby the engagement of the outwardly bulged central portion of the anterior member with the bicep muscle assists in retaining the arm brace in a predetermined position on the upper arm, fastener means mounted on said posterior member for securing said posterior and anterior members snugly together in overlapping relationship.

2. An upper arm brace according to claim 1 wherein said members comprise a molded structure of plastic material and have a plurality of holes therein arranged in a venting pattern, said anterior member having an inside surface of perforated foam material.

3. An upper arm brace according to claim 1 wherein the base of the posterior member has a lower edge extending beyond the side walls of the posterior member to cover the posterior portion of the arm immediately above the elbow, and the base of the anterior member has a lower edge curved upwardly to form a recessed portion received in the crotch between the upper arm and forearm of the wearer.

* * * * *

UNITED STATES PATENT AND TRADEMARK OFFICE
Certificate

Patent No. 4,436,088                        Patented March 13, 1984

On petition requesting issuance of a certificate for correction of inventorship pursuant to 35 USC 256, it has been found that the above-identified patent, through error and without any deceptive intent, improperly sets forth the inventorship. Accordingly, it is hereby certified that the correct inventorship of this patent is Alan R. Finnieston and Joseph B. Zagorski.

Signed and Sealed this 30th Day of September, 1986.

BRADLEY R. GARRIS,
*Office of the Deputy Assistant Commissioner for Patents.*